United States Patent [19]

Luna

[11] Patent Number: 5,150,065
[45] Date of Patent: Sep. 22, 1992

[54] FLEXIBLE HOLDER FOR A CORROSION-DETECTING COUPON

[75] Inventor: Damian J. Luna, Broken Arrow, Okla.

[73] Assignee: Nalco Chemical Company, Naperville, Ill.

[21] Appl. No.: 397,044

[22] Filed: Aug. 22, 1989

[51] Int. Cl.⁵ .............................................. G01R 27/00
[52] U.S. Cl. ..................................... 324/700; 324/724; 324/71.2
[58] Field of Search ................ 324/700, 71.2, 724; 73/86; 204/153.11, 404

[56] References Cited

U.S. PATENT DOCUMENTS

| | | |
|---|---|---|
| 2,664,744 | 1/1954 | Bilhartz et al. |
| 3,104,355 | 9/1963 | Holmes et al. ............ 324/700 X |
| 3,320,570 | 5/1967 | Lied, Jr. ..................... 324/700 X |
| 3,985,624 | 10/1976 | Prevost . |
| 4,120,313 | 10/1978 | Lewis . |
| 4,179,653 | 12/1979 | Davies et al. ................. 324/700 |
| 4,181,882 | 1/1980 | Isaacs et al. . |
| 4,335,072 | 6/1982 | Barnett et al. . |
| 4,697,465 | 10/1987 | Evans et al. . |
| 4,735,095 | 4/1988 | Issel . |
| 4,855,668 | 8/1989 | Crow ............................... 324/700 |

OTHER PUBLICATIONS

Schematic diagram, "Flexible Corrosion Probe" by Nalco Chemical Company, Oct. 24, 1988.

Primary Examiner—Jack B. Harvey
Attorney, Agent, or Firm—Arnold, White & Durkee

[57] ABSTRACT

An apparatus for holding a corrosion-testing coupon within a processing system. The apparatus includes a flexible member having a first end and a second end, the first end of which is adapted for holding the apparatus within the processing system; and an electrically insulative member which is attached to the second end of the flexible member. The electrically insulative member is adapted to hold a corrosion-detecting coupon. Preferably, the flexible member is a flexible corrugated metallic conduit. The apparatus advantageously includes an attachment member, such as a shaft, which is connected to the first end of the flexible member and which is adapted to attach to the processing system; and a sleeve which connects the electrically insulative member to the flexible member.

13 Claims, 4 Drawing Sheets

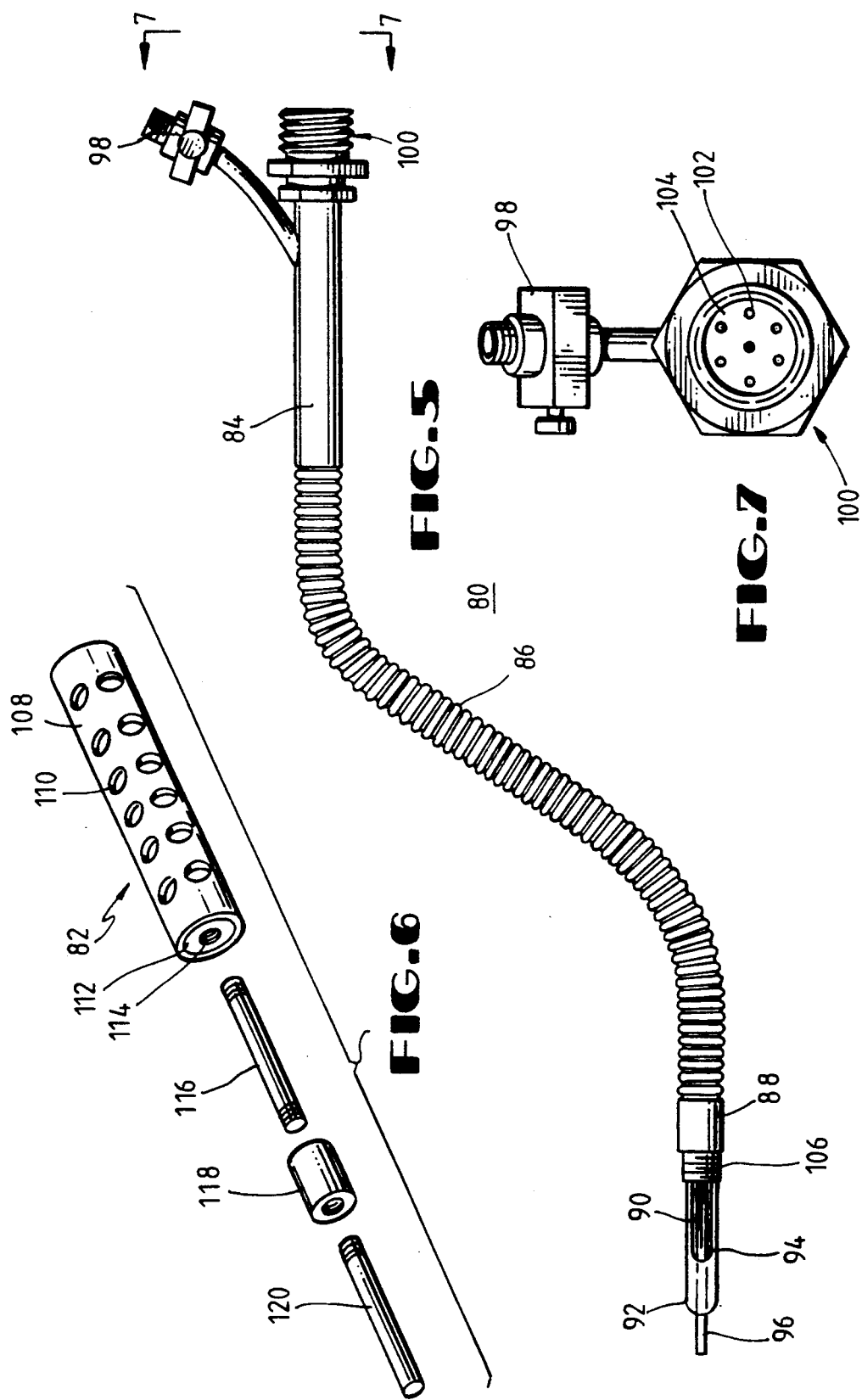

FLEXIBLE HOLDER FOR A CORROSION-DETECTING COUPON

BACKGROUND OF THE INVENTION

1. Field of the Invention

This invention relates generally to corrosion testing equipment, and more particularly to a flexible holder for a corrosion-detecting coupon.

2. Description of the Related Art

Corrosion is a complex phenomenon that may take several different forms. It is usually confined to the surface of a metal, but it sometimes occurs along lines of weaknesses which separate different portions of a metal having a difference in resistance to attack. For instance, electrochemical corrosion takes place between an anodic portion of a metal and cathodic portion of the metal where the flow of electricity from the anodic portion to the cathodic portion promotes corrosion of the metal. One particularly destructive type of electrochemical corrosion is commonly referred to as Galvanic corrosion. Galvanic corrosion occurs when electric current flows from a more active metal to a less active metal where the two types of metals are in contact with one another.

Corrosion is of particular concern in large chemical processing plants, such as oil refineries and petrochemical plants. In oil refineries, for instance, crude oil undergoes fractionation, whereby the crude oil is separated into its different parts or constituents. The resulting fractions include raw gasoline, kerosene, fuel oil, and various types of lubricants. Since some of these fractions are still relatively crude or contain impurities such as sulfur, oxygen, or nitrogen, the fractions must be further treated to provide useful petroleum products. These other treatments include cracking, polymerization, desulfurization, and dehydration, to name a few.

Therefore in view of the extensive refining of crude oil, it is apparent that corrosion must be guarded against in the elaborate plants which refine such oil. During design of the plant, engineers attempt to select the proper materials which will make u the various portions of the plant. However, the large number of chemical reactions which take place at different locations in the plant, and the varying temperatures at which these reactions take place, make it virtually impossible for engineers to select the proper materials at every location in the plant.

Once the plant is constructed, process engineers further attempt to combat corrosion by chemically adjusting the fluidic environment to minimize corrosion. Typical examples would include the addition of inhibitors into aqueous solutions so that the corrosion of iron or steel could be minimized. Chromates, phosphates and silicates minimize corrosion by increasing anodic polarization, and are often called anodic inhibitors. Organic sulfides and amine materials are frequently effective in minimizing the corrosion of iron and steel in an acidic solution because they control cathodic polarization, and are often called cathodic inhibitors.

As implied in the above discussion, and as is well known in the art, it is often quite difficult to determine the composition of fluid at any selected point in a refining process. In an attempt to select the best materials and fluid additives, process engineers test different metals and alloys in laboratories for their corrosion resistance. Although laboratory testing is useful, it is not always practical or convenient to investigate corrosion problems in the laboratory. Laboratory testing is hampered because it is difficult to discover the exact conditions of the corrosive environment and to reproduce them accurately in the laboratory. The exact characteristics of the corrosive environment are particularly difficult to ascertain for a process which involves changes in the composition or other characteristics of the solution as the process is carried out, e.g., distillation and polymerization. Moreover, the presence of a small amount of a particular constituent, such as a corrosion product, may affect the corrosive nature of a substance to a great extent; this too is difficult to reproduce in a laboratory setting.

To overcome problems of laboratory testing and to produce more accurate test results, corrosive testing is carried out at the plant under actual conditions. One popular method for carrying out corrosion testing in the plant environment is commonly referred to as the "electrical-resistance method". By this method, a sample of a metal to be tested is formed into a thin wire or strip and placed into the process fluid. As the test sample corrodes, its cross-section decreases and, therefore, its electrical resistance increases. By periodically monitoring the electrical resistance of the test sample, process engineers are able to determine the rate of corrosion for that particular sample. The electrical-resistance method is advantageous in that corrosion measurement ca be made at any time during the course of the process. However, the test samples are relatively expensive to produce, and the method can give misleading results if a conducting deposit forms on the test sample.

Another commonly used corrosion testing method involves the placement of test specimens, commonly called "coupons", in a process stream. While there is no standard size or shape for corrosion-detecting coupons, they usually weigh about 10 to 50 grams, and preferably have a large surface-to-mass ratio. Several coupons are typically placed on a rod and supported within the process equipment by a bracket which connects the rod to the process equipment. Although this method is advantageous in that it allows coupons of different metallurgies to be placed in substantially the same location within a process stream, the coupons cannot be removed without interrupting the process stream. Therefore, a process engineer must typically wait until a scheduled or unscheduled interruption in the process before the coupons can be removed for testing. Alternatively, a coupon may be placed on a rigid member and inserted into the process equipment via a retraction assembly. The retraction assembly allows the coupon to be withdrawn from the process equipment without interrupting the process.

Another problem with the plant testing methods is that it is often difficult to insert the corrosion-detecting coupon at the desired location within the process system. This is especially true for retractable coupons because of the difficulties involved with placement and orientation of a retraction assembly in many areas of a process system. For instance, in distillation towers fluid flows onto and through a plurality of horizontally "stacked" trays. Therefore, the trays are subject to corrosion. However, due to the design of a distillation tower, it is difficult to place a corrosion-detecting coupon, particularly a retractable coupon, directly in the fluid which is on the trays. Hence, corrosion testing in distillation towers renders less than accurate results.

SUMMARY OF THE INVENTION

In accordance with one aspect of the present invention, an apparatus for holding a corrosion-testing coupon within a processing system is provided. The apparatus includes a flexible member having a first end and a second end, the first end of which is adapted for holding the apparatus within the processing system; and an electrically insulative member which is attached to the second end of the flexible member. The electrically insulative member is adapted to hold a corrosion-detecting coupon.

Preferably, the flexible member is a flexible corrugated metallic o Teflon conduit. The apparatus advantageously includes an attachment member, such as a shaft, which is connected to the first end of the flexible member and which is adapted to attach to the processing system; and a sleeve which connects the electrically insulative member to the flexible member.

In accordance with another aspect of the present invention, an apparatus for testing a plurality of corrosion indicating parameters within a processing system is provided. The apparatus includes a hollow tubular shank having a first end and a second end, and a hollow flexible shaft having a first end and a second end. The first end of the flexible shaft is attached to the second end of the tubular shank. A hollow tubular sleeve having a first end and a second end is attached by its first end to the second end of the flexible shaft, thereby forming a passageway extending from the first end of the tubular shank to the second end of the tubular sleeve. A wire is disposed in the passageway and forms a resistive loop which protrudes from the second end of the tubular sleeve. An electrical outlet is connected to the first end of the tubular shank, and the wire begins and ends at the electrical outlet. A sheath is attachable to the second end of the tubular sleeve and is adapted to encompass the resistive loop when attached. An electrically insulative member is attached to the sheath, and is adapted to hold a corrosion-testing coupon.

In accordance with yet another aspect of the present invention, a method for allowing a corrosion-testing coupon to be placed on a tray in a distillation tower is provided. The method includes the steps of attaching a coupon to an electrically insulative member which is disposed on a first end of a flexible shaft, and inserting the first end of the flexible shaft into the distillation tower at a location which is above the tray. The flexible shaft is of sufficient length to allow the coupon to reach the tray during insertion of the flexible shaft. The method further includes the step of connecting a second end of the flexible shaft to a structural support associated with the distillation tower.

Preferably, the step of connecting includes the steps of attaching a connecting member to the second end of the flexible shaft, and attaching the connecting member to the structural support. The step of inserting preferably includes the steps of forming a predefined channel which provides access to a interior portion of the distillation tower, and moving the flexible shaft through the predefined channel and into the distillation tower. Alternatively, the step of connecting may include the steps of attaching a rigid shaft to the second end of the flexible shaft, and holding the rigid shaft within the predefined channel. Preferably, the predefined channel is openable and closeable, and allows the corrosion-testing coupon to be inserted into and withdrawn from the distillation tower during the distillation operation.

BRIEF DESCRIPTION OF THE DRAWINGS

Other advantages of the invention will become apparent upon reading the following detailed description and upon reference to the drawings in which:

FIG. 5 illustrates a second embodiment of the flexible coupon holder in accordance with the present invention;

FIG. 6 is a perspective view of an end portion of the second embodiment of the flexible coupon holder in accordance with/the present invention; and FIG. 7 is an end view taken generally along line 7—7 in FIG. 5.

Figure 1:
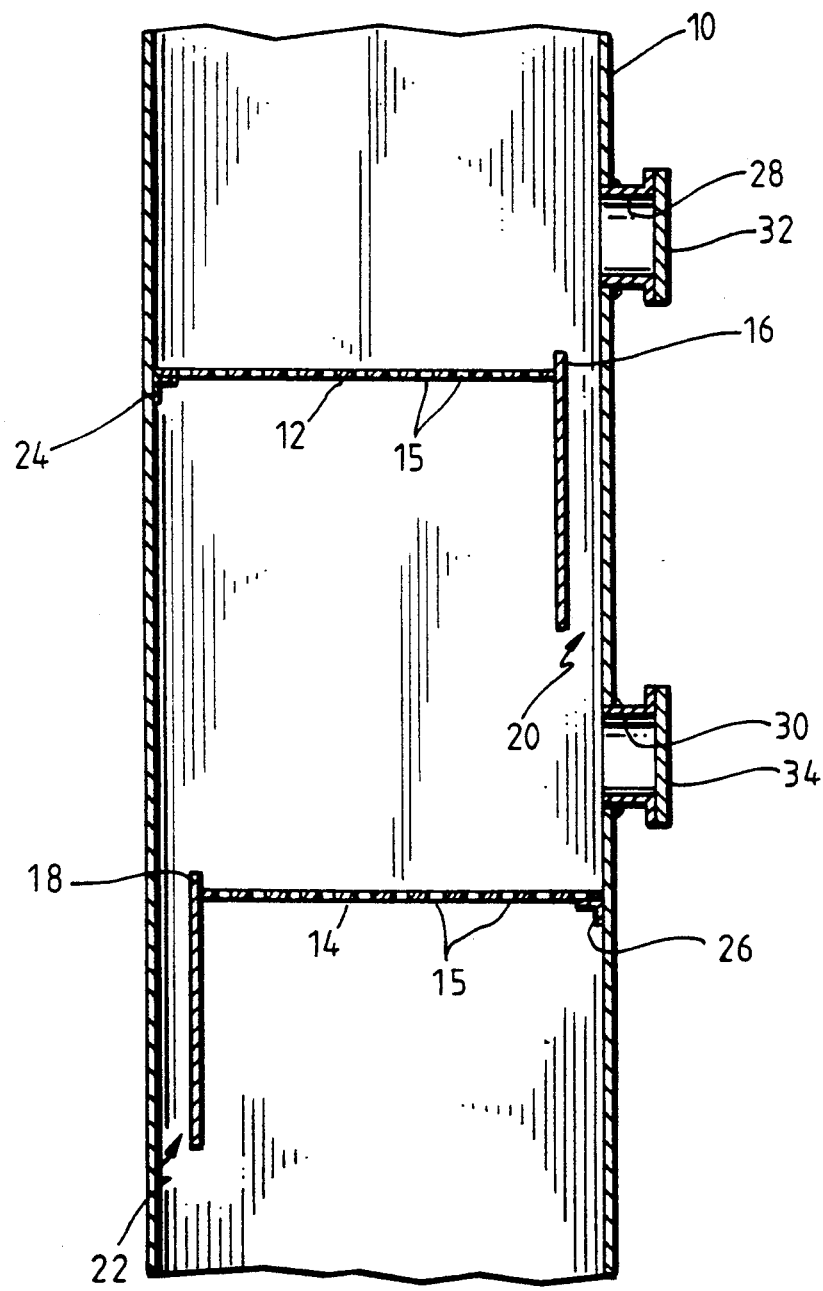
FIG. 1 illustrates a portion of a distillation tower having trays disposed therein.

While the invention is susceptible to various modifications and alternative forms, specific embodiments thereof have been shown by way of example in the drawings and will be described in detail herein. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENTS

Returning now to the drawings, an referring initially to FIG. 1, a vertical cross-section of a distillation tower 10 is shown. The section of the distillation tower 10 includes two trays, an upper tray 12 and a lower tray 14. The trays 12, 14 in the distillation tower 10 include means for retaining fluid on the trays 12, 14 for a predetermined period of time, such as upwardly extending peripheral lips 16, 18; means for allowing vapor to penetrate upwardly through the trays 12, 14 while the liquid is being retained thereon, such as bubble-caps (not shown) or perforations 15; and means for allowing the fluid to pass downwardly within the distillation tower 10 to the next tray, such as downcomer weirs 20, 22, so that the fluid may be retained on the next tray for a second predetermined period of time while the vapor passes through the tray and through the fluid thereon.

The walls of the distillation tower 10 are typically made of high carbon steel which is approximately one inch in thickness, and the trays 12, 14 are secured within the distillation tower 10 by means of mounting brackets 24, 26. The trays 12, 14 are typically made of a corrosion-resisting alloy which has been selected to resist corrosion from the chemicals and fluids in the distillation tower 10. If a tray 12, 14 in the distillation tower 10 corrodes, it will allow too much liquid to flow down through the downcomers 20, 22 or through the perforations within the tray, or it may allow too much vapor to flow upwardly through the perforations. Corrosion of the trays 12, 14 adversely affects the distillation process, and, thus, lowers the quality of the refined end-products. Since the trays 12, 14 corrode and occasionally need to be replaced, manways 28, 30 are installed in the sides of the distillation tower 10 so that corroded trays may be removed and replaced with new trays. The manways 28, 30 are sealed by manway covers 32, 34.

Figure 2:
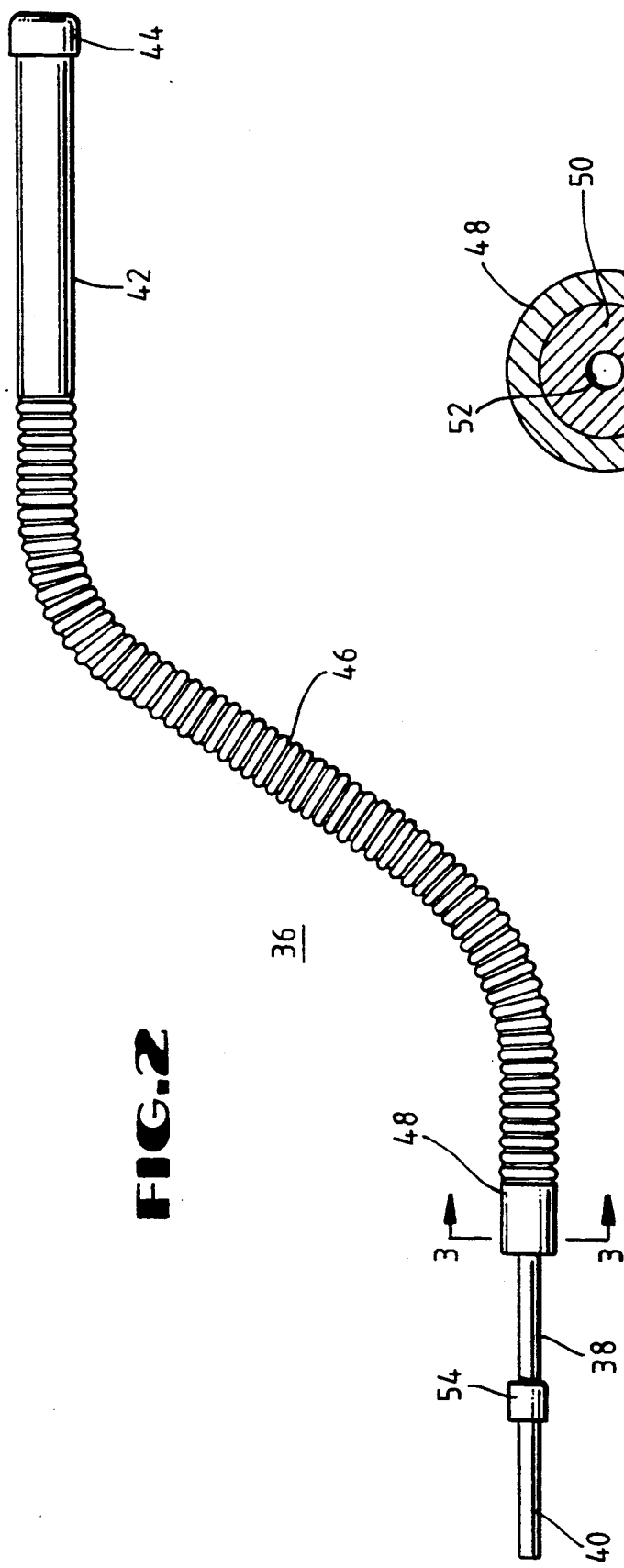
FIG. 2 one embodiment of a flexible coupon holder in with the present invention.
Figure 3:
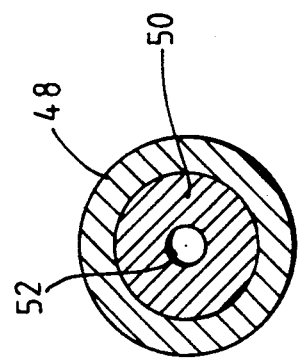
FIG. 3 a cross-sectional view taken generally along line 3—3 in FIG. 2.

Referring now to FIGS. 2 and 3, a flexible coupon holder 36 for enabling corrosion-detecting coupons 38, 40 to be placed on a tray 12, 14 in a distillation tower 10 is provided. The flexible coupon holder 36 includes a tubular shank 42 having a handle 44 on one end thereof which allows the flexible coupon holder 36 to be inserted and withdrawn from the distillation tower 10, as will be subsequently described. Connected to the tubular shank 42, opposite the handle 44, is an elongated flexible member 46, which is preferably a flexible metal conduit or a flexible Teflon conduit.

A sleeve 48 is attached to the other end of the flexible member 46, and, as shown in FIG. 3, the sleeve 48 includes an insert 50 made from electrically insulative material, such as Teflon. The insert 50 includes a threaded bore 52 which is adapted to accommodate external threads (not shown) on one end of the coupon 38. The electrically insulative insert 50 prevents Galvanic corrosion between the metallic sleeve 48 and the metallic coupon 38. Alternatively, the entire sleeve 48 may be made out of an electrically insulative material which is fastened to one end of the flexible member 46. As shown in FIG. 2, the coupon 38 is connected to another coupon 40 by a washer 54, which is preferably made of an electrically insulative material. Again, the electrically insulative washer 54 is designed to prevent metal-to-metal contact between the coupons 38 and 40, so that Galvanic corrosion does not occur between the coupons 38 and 40. However, in some cases Galvanic corrosion measurements are desired, and, in those cases, the electrically insulative washer 54 may be replaced by a connection member which allows such metal-to-metal contact.

The flexible member 46 allows the coupons 38, 40 to lie directly on one of the trays 12, 14 when the flexible coupon holder 36 is placed within the distillation tower 10 at a location above the appropriate selected tray 12, 14. When the flexible coupon holder 36 is inserted into the distillation tower 10, the coupons 38, 40 are suspended by the flexible member 46 until they come to rest on the selected tray 12, 14. The length of the flexible member 46 is selected so that the coupons will reach the selected tray 12, 14 during insertion of the flexible coupon holder 36.

Figure 4:
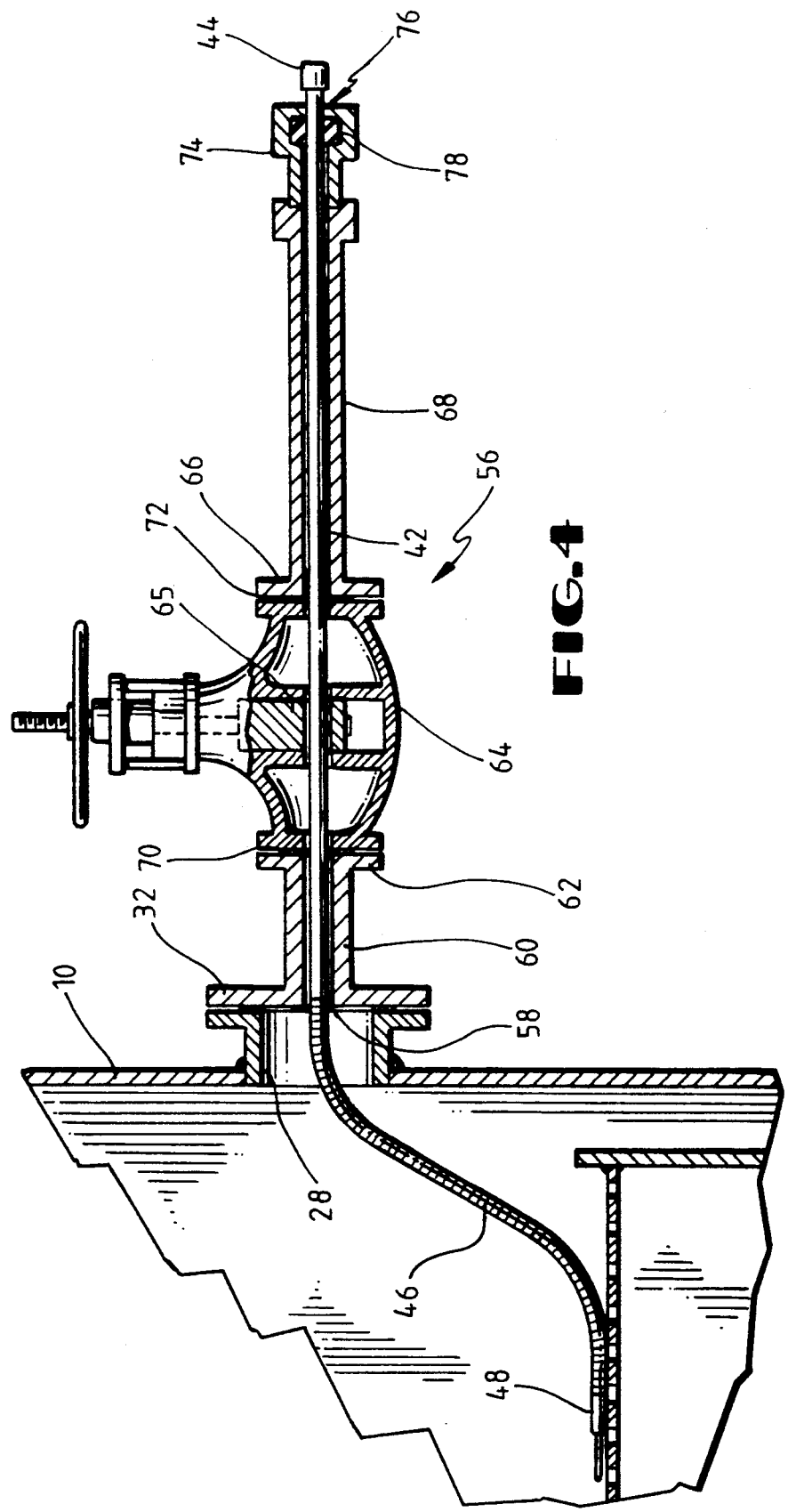
FIG. 4 illustrates an assembly which allows the flexible coupon holder of the present invention inserted and withdrawn from process equipment.

Preferably, the flexible holder 36 can be inserted into the distillation tower 10 and removed from the distillation tower 10 at any time. To place a coupon on tray 12, it is convenient to attach a sealed valve assembly 56 to the manway cover 32, as shown in FIG. 4. An aperture 58 is formed in the manway cover 32, and one end of a connecting pipe 60 is welded onto the manway cover 32 concentric with the aperture 58, so that a passageway is formed into the distillation tower 10. The opposite end of the pipe 60 includes a flange 62 to which one end of a gate valve 64 is attached, preferably by bolting. The gate valve 64 includes a valve body 65 which is adapted to open or close the passageway. The other end of the gate valve 64 is attached to a flange 66 which is formed at one end of an extension tube 68. Of course, since fluid is flowing within the distillation tower 10, seals 70, 72 are provided between each end of the gate valve 64 and the respective flanges 62, 66. Preferably, the other end of the extension tube 68 is adapted to be screw-threadably attached to a packing gland 74. As constructed, the valve assembly 56 forms a channel 76 which is adapted to accept the flexible coupon holder 36.

To insert the flexible coupon holder 36 into the distillation tower 10, the coupons 38, 40, the sleeve 48 and the flexible member 46 are inserted into the extension tube 68 and the packing gland 74 is screwed onto the end of the extension tube 68. The packing gland 74 includes an annular seal 78 which effectively seals around the tubular shank 42 to prevent fluid from within the distillation tower 10 from escaping through the channel 76 when the gate valve 64 is open. Initially, however, the valve body 65 is closed so that no fluid can escape into the extension tube 68 from the distillation tower 10. Therefore, the extension tube 68 should have sufficient length to accommodate the length of the flexible member 46, the sleeve 48 and any coupons attached thereto, so that the packing gland 74 can be attached to the extension tube 68. Once the packing gland 74 is attached to extension tube 68, the valve 64 is opened and the tubular shank 42 is pushed axially within the packing gland 74 toward the distillation tower 10 so that the coupons and the flexible member 46 extend into the distillation tower 10. The axial movement of the shank 42 should be sufficient to allow coupons 38, 40 at the end of the flexible member 46 to reach the selected tray 12, 14.

To withdraw the flexible holder 36 so that coupons may be inspected, the above procedure is reversed. The shank 42 is pulled outwardly away from the distillation tower 10 until the flexible member 46, sleeve 48 and any coupons attached thereto are clear of the valve body 65 so that gate valve 64 may be closed. Although sliding the shank 42 through the annular seal 78 poses no sealing problems, sliding the flexible member 46 through the annular seal 78 may injure the annular seal 78. Therefore, the packing gland 74 is preferably removed from the extension tube 68 so that the coupons may be inspected. Alternatively, if the flexible member 46 would not harm the annular seal 78, the tubular shank 42 could be made shorter, as could the extension tube 68, because the flexible member 46 and any coupons attached thereto could be removed from the valve assembly 56 by drawing them through the annular seal 78.

To detect a variety of corrosion-indicating parameters, a flexible probe 80 which includes a coupon holder 82 is used, as shown in FIGS. 5–7. The flexible probe 80 includes a hollow tubular shank 84, one end of which is attached to a hollow flexible member 86, such as a hollow corrugated conduit. The other end of the hollow flexible member 86 is attached to a hollow sleeve 88 which houses various types of sensors. For instance, a thermocouple 90 functions as a temperature sensor, and corrosion may be tested using the electrical-resistance method by measuring the resistance of a wire loop 92, which is composed of a specified material. Furthermore, a second wire loop 94 is used for temperature compensation to insure that the temperature sensed by the thermocouple 90 is accurate. In addition to these electrical sensors, a hollow tube 96, preferably made of plastic, extends from a coupling valve 98, through the hollow tubular shank 84 and hollow flexible member 86, and protrudes from the sleeve 88. During processing, the coupling valve 98 may be opened to withdraw a fluid sample through the tube 96. A portion of the hollow sleeve 88 is filled with a sealing compound to seal around the sensors and to prevent fluid from entering the hollow portions of the flexible probe 80.

An electrical outlet 100 is attached to the distal end of the hollow tubular shank 84 so that a corrosometer can be attached for reading the resistivity of the wire loop 92, and so that the temperature of the thermocouple 90 can be read using an appropriate instrument. The outlet 100 is shown in FIG. 7 as having a plurality of outwardly extending connection pins 102, and a threaded sleeve 104 to facilitate attachment of these monitoring instruments.

The coupon holder 82 is adapted to be attached to the sleeve 88, preferably by threading onto the threaded section 106 of the sleeve 88. The coupon holder 82 preferably includes a hollow sheath 108 which has a plurality of perforations 110 formed therein. The hollow sheath 108 with the perforations 110 forms a shield which allows fluid flow across the sensors and protects the sensors from undue physical damage. An insert 112 made of electrically insulative material is placed in the end of the sleeve 108 opposite the internally threaded end. The insert 112 includes a threaded counterbore 114 which is adapted to screw-threadably accept one end of threaded coupon 116. Using washers, such as an electrically insulative washer 118, a plurality of coupons, such as coupon 120, can be attached to the coupon holder 82.

I claim:

1. An apparatus for testing a plurality of corrosion indicating parameters within a processing system, said apparatus comprising:
   a hollow tubular shank having a first end and a second end;
   a hollow flexible shaft having a first end and a second end, the first end of said flexible shaft being attached to the second end of said tubular shank;
   a hollow tubular sleeve having a first end and a second end, the first end of said tubular sleeve being attached to the second end of said flexible shaft, thereby forming a passageway extending from the first end of said tubular shank to the second end of said tubular sleeve;
   a wire being disposed in said passageway and forming a resistive loop which protrudes from the second end of said tubular sleeve;
   an electrical outlet being connected to the first end of said tubular shaft, said wire beginning and ending at said electrical outlet;
   a sheath having a first end and a second end, said first end of said sheath being attachable to the second end of said tubular sleeve, said sheath being adapted to encompass said resistive loop when attached; and
   an electrically insulative member being attached to said second end of said sheath, said electrically insulative member being adapted to hold a first end of a corrosion-testing coupon such that a second end of said corrosion-testing coupon extends axially outwardly from said second end of said sheath.

2. The apparatus, as set forth in claim 1, wherein the resistivity of said resistive loop is measured as an indication of corrosion of said resistive loop.

3. The apparatus, as set forth in claim 2, wherein an instrument is connected to said electrical outlet to perform said measurement.

4. The apparatus, as set forth in claim 1, wherein said sheath is adapted to diffuse fluid flow about said resistive loop.

5. The apparatus, as set forth in claim 4, wherein said sheath includes a plurality of apertures formed therein.

6. The apparatus, as set forth in claim 1, further comprising:
   a thermocouple which protrudes from the second end of said tubular sleeve and which is electrically connected to said electrical outlet.

7. The apparatus, as set forth in claim 1, further comprising:
   a hollow tube which extends through said passageway and which protrudes from the second end of said tubular sleeve; and
   a hollow tube which extends through said passageway and which protrudes from the second end of said tubular sleeve; and
   a valve being connected to an end of said tube proximate the first end of said tubular shank, said valve being adapted to open and close to respectively allow and prevent fluid from within said processing system from exiting through said tube.

8. A method for allowing a corrosion-testing probe, including a corrosion-testing coupon, to be placed on a tray in a distillation tower, comprising the steps of:
   attaching said coupon to an electrically insulative member which is disposed on a first end of a tubular sheath;
   attaching a second end of said tubular sheath to a first end of a flexible shaft, said first end of said flexible shaft having a sensor protruding outwardly therefrom, said tubular sheath being adapted to substantially encompass said sensor;
   inserting the first end of said flexible shaft into said distillation tower at a location which is above said tray, said flexible shaft being of sufficient length to allow said coupon to reach said tray during insertion of said flexible shaft; and
   connecting a second end of said flexible shaft to a structural support associated with said distillation tower, the second end of said flexible shaft having an electrical outlet being connected thereto which extends outside said distillation tower, said electrical outlet being adapted to allow monitoring of said sensor.

9. The method, as set forth in claim 8, wherein said step of connecting comprises the steps of:
   attaching a connecting member to the second end of said flexible shaft; and
   attaching said connecting member to said structural support.

10. The method, as set forth in claim 8, wherein said step of inserting comprises the steps of:
    forming a predefined channel which provides access to an interior portion of said distillation tower; and
    moving said flexible shaft having said coupon attached thereto through said predefined channel and into said distillation tower.

11. The method, as set forth in claim 10, wherein said step of connecting comprises the steps of:
    attaching a rigid shaft to the second end of said flexible shaft; and
    holding said rigid shaft within said predefined channel.

12. The method, as set forth in claim 10, wherein said predefined channel is openable and closeable.

13. The method, as set forth in claim 12, wherein said predefined channel allows said corrosion-testing coupon to be inserted into and withdrawn from said processing system during processing.

* * * * *

UNITED STATES PATENT AND TRADEMARK OFFICE
CERTIFICATE OF CORRECTION

PATENT NO. : 5,150,065

DATED : September 22, 1992

INVENTOR(S) : Damian J. Luna

It is certified that error appears in the above-identified patent and that said Letters Patent is hereby corrected as shown below:

Column 1, line 42, "u" should be --up--.

Column 2, line 28, "ca" should be --can--.

Column 3, line 14, "o" should be --or--.

Column 4, line 20, after "with" delete --/--.

Column 8, lines 11-13, delete --a hollow tube which extends through said passageway and which protrudes from the second end of said tubular sleeve; and--.

Signed and Sealed this

Thirtieth Day of November, 1993

Attest:

BRUCE LEHMAN

Attesting Officer

Commissioner of Patents and Trademarks